US012232900B2

(12) United States Patent
Zheng et al.

(10) Patent No.: US 12,232,900 B2
(45) Date of Patent: Feb. 25, 2025

(54) INTERACTIVE CONTOUR REFINEMENTS FOR DATA ANNOTATION

(71) Applicant: Shanghai United Imaging Intelligence Co., LTD., Shanghai (CN)

(72) Inventors: Meng Zheng, Cambridge, MA (US); Elena Zhao, Cambridge, MA (US); Srikrishna Karanam, Cambridge, MA (US); Ziyan Wu, Cambridge, MA (US); Terrence Chen, Cambridge, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 509 days.

(21) Appl. No.: 17/560,492

(22) Filed: Dec. 23, 2021

(65) Prior Publication Data

US 2023/0200767 A1    Jun. 29, 2023

(51) Int. Cl.
*A61B 6/46* (2024.01)
*G06T 7/149* (2017.01)

(52) U.S. Cl.
CPC .............. *A61B 6/468* (2013.01); *A61B 6/469* (2013.01); *G06T 7/149* (2017.01); *G06T 2207/10081* (2013.01); *G06T 2207/10088* (2013.01); *G06T 2207/30096* (2013.01); *G06T 2207/30204* (2013.01)

(58) Field of Classification Search
CPC ......... A61B 6/468; A61B 6/469; A61B 6/501; A61B 6/5217; G06T 7/149; G06T 2207/10081; G06T 2207/10088; G06T 2207/30096; G06T 2207/30204; G06T 7/12
See application file for complete search history.

(56) References Cited

U.S. PATENT DOCUMENTS

| | | | | |
|---|---|---|---|---|
| 9,311,705 | B1* | 4/2016 | Fotin | G06T 7/74 |
| 2007/0147700 | A1* | 6/2007 | Jeong | G06T 11/60 |
| | | | | 382/199 |
| 2008/0123914 | A1* | 5/2008 | De Bliek | G06T 7/12 |
| | | | | 382/128 |
| 2008/0267468 | A1* | 10/2008 | Geiger | G01S 7/52036 |
| | | | | 382/128 |
| 2013/0310690 | A1* | 11/2013 | Chang | A61B 8/485 |
| | | | | 600/443 |
| 2020/0093464 | A1* | 3/2020 | Martins | A61B 8/12 |
| 2023/0071291 | A1* | 3/2023 | Chen | G06V 10/44 |

OTHER PUBLICATIONS

Wu et al. (Automatic glioma segmentation based on adaptive superpixel 2019 (Year: 2019).*

* cited by examiner

*Primary Examiner* — Wassim Mahrouka
(74) *Attorney, Agent, or Firm* — Zhong Law, LLC

(57) ABSTRACT

An automated process for data annotation of medical images includes obtaining image data from an imaging sensor, partitioning the image data, identifying an object of interest in the partitioned image data, generating an initial contour with one or more control points with respect to the object of interest, identifying a manual adjustment of one of the control points, automatically adjust a position of at least one other control point within a predetermined range of the manually adjusted control point to a new position, the new position of the at least one other control point and manually adjusted control point defining a new contour, and generating an updated image with the new contour and corresponding control points.

18 Claims, 7 Drawing Sheets

INTERACTIVE CONTOUR REFINEMENTS FOR DATA ANNOTATION

FIELD

The aspects of the disclosed embodiments relate generally to data annotation, and more particularly to automated contour adjustment for data annotation.

BACKGROUND

Data annotation is the process of labelling data used for machine learning. The data can be available in various formats like text, video or images. In the medical imaging field, for example, Artificial intelligence (AI) and machine learning provides advantages by making it easier to more accurately predict results with greater accuracy and speed. However, to create such automated applications or machines, extensive amounts of training data sets are required. For supervised machine learning, labelled data sets are required to enable the machine to learn the input patterns and provide accurate predictions.

In data annotation processes, the initial given contour(s), also referred to as boundaries or edges, of the object of interest may not be satisfactory. This often requires the user to exhaustively adjust the control points to obtain satisfactory contour annotations. Such manual intervention is time intensive, prone to error and generally inefficient.

Accordingly, it would be desirable to provide methods and apparatus that address at least some of the problems described above.

SUMMARY

The aspects of the disclosed embodiments are directed to automated control point adjustment in data annotation. This and other advantages of the disclosed embodiments are provided substantially as shown in, and/or described in connection with at least one of the figures, as set forth in the independent claims. Further advantageous modifications can be found in the dependent claims.

According to a first aspect, the disclosed embodiments are directed to an apparatus for automated control point adjustment in data annotation. The apparatus includes a processor that is configured to automatically adjust the positioning of control points identifying the contours of a medical image for a segmentation mask based on a user input and the image partitions. This reduces the human labelling effort as compared to conventional methods.

In a possible implementation form the apparatus is configured to receive medical image data and identify contours of one or more objects of interests in the medical image data. The apparatus is configured to partition the medical image data in an area within at least the initial contours based on one or more characteristics of the medical image data. The apparatus is further configured to generate one or more control points on the contour of the one or more objects of interest. An adjustment of a position of a first control point is detected. The apparatus is configured to automatically adjust a position of at least one control point adjacent to the first control point based on the detected adjustment of the first control point.

In a possible implementation form, the original image, control points and contour are presented on a display of a user interface.

In a possible implementation form, the at least one adjacent control point is within a predetermined distance from the first control point.

In a possible implementation form, the at least one adjacent control point includes all control points within a predetermined distance from the first control point.

In a possible implementation form, a distance and direction of the adjustment of the position of the first control point is identified.

In a possible implementation form the at least one adjacent control point is moved in a same direction as a movement of the first control point.

In a possible implementation form, a distance of a movement of the at least one adjacent control point is proportional to a distance of a movement of the first control point.

In a possible implementation form, a distance of a movement of the at least one adjacent control point is a same distance as a movement of the first control point.

In a possible implementation form, the at least one adjacent control point is moved in a same direction as the movement of the first control point until a next partition line associated with the object of interest is detected.

In a possible implementation form, the initial contour is automatically updated to a next contour relative to the object of interest following the automatic adjustment of the at least one adjacent control point.

In a possible implementation form the adjustment of the at least one adjacent control point is a pixel based adjustment.

In a possible implementation form, the partitioning within the initial contour(s) can be automatically generated based on geometry information of the object of interest.

In a possible implementation form the output of the partitioning can be one or more of coarse or fine partitioning.

In a possible implementation form the degree of movement of the at least one adjacent control point during the automatic adjustment of the control points and contour(s) depends on a granularity or degree of fineness of the partitioning.

In a possible implementation form, the control points are generated for the initial contour(s) based on one or more characteristics of the points along the initial contour.

In a possible implementation form, the number of control points generated for the contour can be adjustable based on annotation requirements or user input.

In a possible implementation form, the number of automatically adjusted control points can be specified by the user or automatically defined based on one or more of a size and/or shape of the object of interest and characteristics of the initial contour(s).

In a possible implementation form, the adjusted control points can be further adjusted by the user.

In a possible implementation form, the medical image data is two dimensional image medical image data.

In a possible implementation form, the medical image data is three dimensional image medical image data.

In a possible implementation form, the medical image data comprises slices of data, where the slices are loaded and annotated one by one.

In a possible implementation form a segmentation mask is output after the automatic adjustment of the control points.

According to a second aspect, the disclosed embodiments are directed to a method. In one embodiment, the method includes automatically adjusting the positioning of control points identifying the contours of a medical image for a segmentation mask based on a user input and the image partitions. This reduces the human labelling effort as compared to conventional methods.

According to a third aspect, the disclosed embodiments are directed to a computer program product embodied on a non-transitory computer readable medium, the computer program product comprising computer instructions that, when executed on at least one processor of a system or an apparatus, is configured to perform the possible implementation forms described herein.

According to a fourth aspect, the disclosed embodiments are directed to a device comprising means for performing the possible implementation forms described herein.

These and other aspects, implementation forms, and advantages of the exemplary embodiments will become apparent from the embodiments described herein considered in conjunction with the accompanying drawings. It is to be understood, however, that the description and drawings are designed solely for purposes of illustration and not as a definition of the limits of the disclosed invention, for which reference should be made to the appended claims. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

BRIEF DESCRIPTION OF THE DRAWINGS

In the following detailed portion of the present disclosure, the invention will be explained in more detail with reference to the example embodiments shown in the drawings, in which.

DETAILED DESCRIPTION OF THE DISCLOSED EMBODIMENTS

The following detailed description illustrates exemplary aspects of the disclosed embodiments and ways in which they can be implemented. Although some modes of carrying out the aspects of the disclosed embodiments have been disclosed, those skilled in the art would recognize that other embodiments for carrying out or practising the aspects of the disclosed embodiments are also possible.

Figure 1:
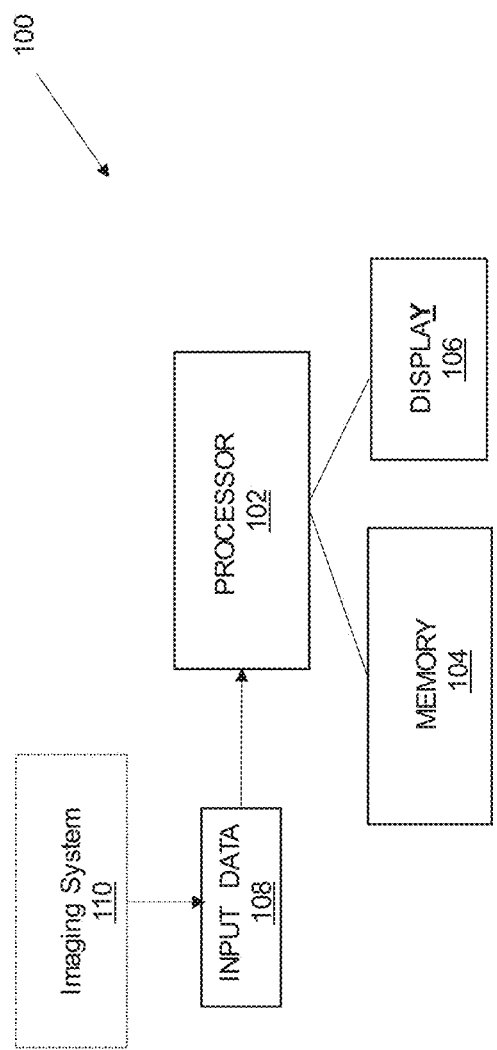
FIG. 1 is a block diagram of an apparatus incorporating aspects of the disclosed embodiments.

Referring to FIG. 1, a schematic block diagram of an exemplary apparatus 100 for automated contour adjustment for data annotation is illustrated. The aspects of the disclosed embodiments are generally directed to automatically adjusting a position of one or more control points and initial contour(s) based on user input and characteristics of an object or region of interest. The need for manual intervention is minimized which improves annotation efficiency.

In one embodiment, the apparatus 100 can be implemented as a tool in a medical image or medical image annotation apparatus or system 110. The apparatus 100 can be communicatively coupled to the imaging system 110 as shown in the example of FIG. 1. In alternative embodiments, the apparatus 100 can be embodied in or part of the imaging system 110. Examples of such imaging systems can include, but are not limited to x-ray imaging systems, medical resonance imaging (MRI) systems, and computed tomography (CT) systems. Although medical imaging systems are generally referred to herein, the aspects of the disclosed embodiments are not so limited. In alternate embodiments, the aspects of the disclosed embodiments can be implemented in any imaging system where annotation of contours of an object or region of interest is desired.

Figure 2:
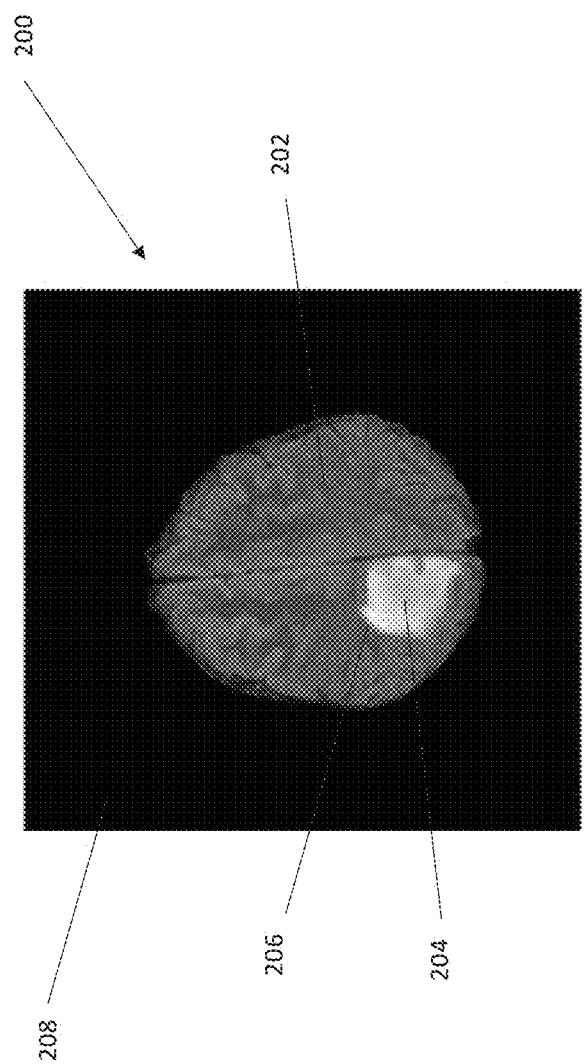
FIG. 2 illustrates exemplary medical image data to be annotated by an apparatus incorporating aspects of the disclosed embodiments.

As used herein, the term "annotation" generally refers to defining the edges or boundaries of an object or region of interest in an image. Referring to FIG. 2, the image 200 is the scan of a body organ, which in this example is a scan of brain tissue. An object or region of interest 204 in this example is shown as the white or lighter area within or against the backdrop of the overall shape of the organ 202. For purposes of the description herein, the area or region 204 will be referred to as the "object of interest."

As an example, for a given a sequence of CT/MRI scan images of a patient with a tumor, the annotation tool of the disclosed embodiments provides utilities for the annotator to mark the tumor region out in the scan images. In one embodiment, the output can be a binarized mask having a same size as the scan image 200, with a "1" indicating a tumor region and a "0" indicating a normal, or non-tumor region.

As shown in FIG. 2, a contour 206 identifies the boundary or edges of the object of interest 204. As will be generally understood, identification of the boundaries or edges of the object of interest 204 is necessary for accurate assessment and labelling purposes.

In certain imaging processes, the boundaries or edges of the object of interest 204 will be marked with a line or other suitable marker. For the purposes of the description herein, this marking or definition of the boundary or edges will be referred to as "contour 206."

As will be described further herein, control points or markers can be commonly used to identify and annotate the contour 206 of the object of interest 204. When a contour 206 is not accurately marked by a line or control point, the positions of the control points can be adjusted to more accurately define the contour 206. The aspects of the disclosed embodiments are directed to the automatic adjustment of control point positions and definition of the contour 206.

Referring again to FIG. 1, in one embodiment the apparatus or system, includes at least one processor 102. The processor 102 is configured to receive image data 108 as an input. As generally described herein, the image data 108 is medical image data such as the image 200 of FIG. 2.

In one embodiment, the image data 108 is received from an imaging system 110. Although the processor 102 and apparatus 100 of FIG. 1 are shown as external to the imaging system 110, the aspects of the disclosed embodiments are not so limited. In alternate embodiments, the apparatus 100 and processor 102 can be a component of the imaging system 110.

Figure 3:
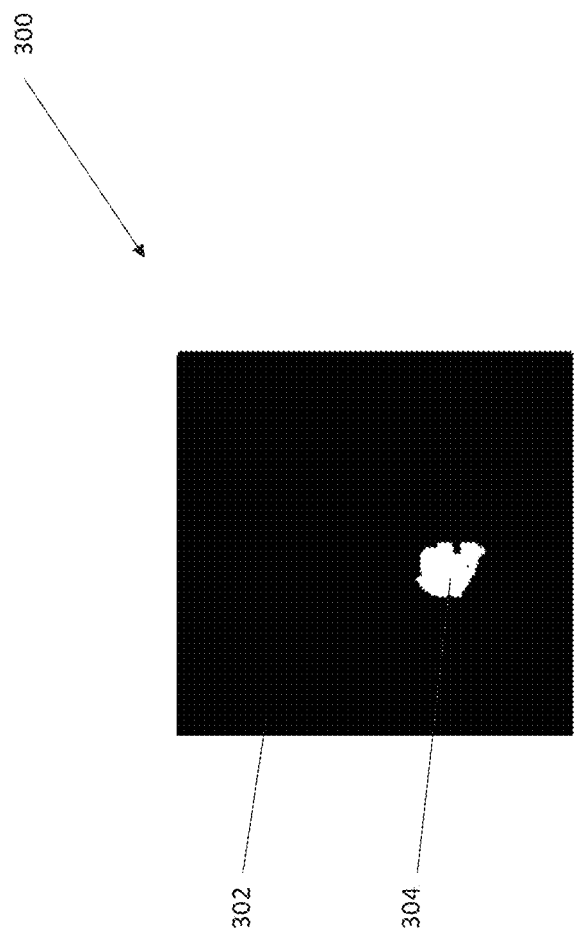
FIG. 3 illustrates an exemplary segmentation mask of the medical image data mage data of FIG. 2 generated by an apparatus incorporating aspects of the disclosed embodiments.

In one embodiment, the processor 102 is configured to initially partition the input image data 108 based on a segmentation mask. One example of a segmentation mask is shown in FIG. 3. In this example, the segmented image 300 includes a dark, background region 302, and a light or white region 304. The white region 304 generally encompasses the object of interest 204 shown in FIG. 2. As will be described further in conjunction with FIG. 4A, the area 304 will be partitioned and control points generated. The segmentation process described herein generally comprises any suitable image segmentation process.

Figure 4:
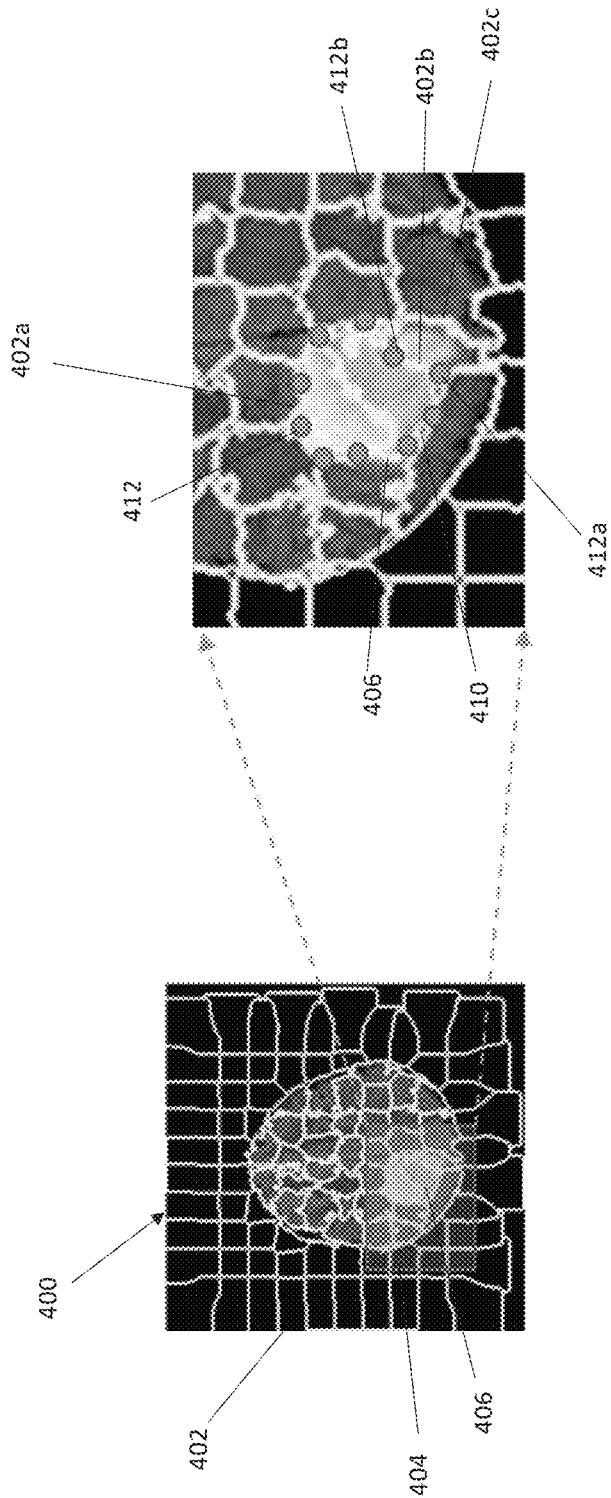
FIG. 4A illustrates an exemplary partitioning of the medical image data of FIG. 2.
FIG. 4B illustrates an exploded view of the object of interest of FIG. 4A.

An example of partitioned input image data 400 is shown in FIG. 4A. As can be seen from this example, the partitioning of the input image data 108 of FIG. 2 generally results in a partitioned image 400 with a series of grid-like lines 402. In the example of FIG. 4A, the grid-like lines 402 are non-linear and generated by a partitioning algorithm. The partitioning algorithm is generally configured to generate the grid-like lines 402 based on pixel features of the input image 108, shown as scanned image 404 in FIG. 4A. The white or lighter colored area 406 in the example of FIG. 4A is the object of interest. Other considerations in the generation of the grid-like lines 402 can include, but are not limited to, the geometric shape and size of the object of interest 406.

Referring also to FIG. 4B, in one embodiment, an initial contour 410 identifies a boundary or edge region of the object of interest 406. As shown in FIG. 4B, one or more control points or markers 412 are generated and used to identify or mark the contour 410 based on the partitioning. The control points 412 are generally configured to provide a visual identification of the contour 410 to a user.

The number of control points 412 shown in FIG. 4B is merely exemplary. In alternate embodiments, the number of control points 412 can be any suitable number. For example, in one embodiment the number of control points 412 is set by the user.

In one embodiment, the partitioned input image 400 with the control points 412 can be presented on a display 106 of the apparatus 100. In one embodiment, the display 106 can be part of a user interface of the apparatus 100 that allows the annotator to interact and annotate the image 400 as is generally described herein. In one embodiment, the apparatus 100 can include suitable tools, such a joystick, touch pen, mouse or other cursor device that will allow the annotator to reposition the control points 412 as is described herein. The aspects of the disclosed embodiments are configured to allow the annotator to click on points in the image 400, draw lines on the image 400, as well as drag or move points and lines on or in the image 400. In one embodiment, the display or user interface 106 comprises a touch screen or touch sensitive device that allows the annotator to interact with the image 400 as is generally described herein.

For example, in one embodiment, the input image data 108 comprises CT/MRI scan images. The input image data 108 to be annotated will typically be in the form of a sequence of grayscale images. When the user or annotator starts to annotate the scanned images, these scanned images are loaded and shown to the annotator via a computer screen or user interface 104, as is shown in the example of FIG. 4A. The user can select a suitable tool from a utility or toolbox provided by the apparatus 100, and use the tool to annotate the image 400 as is generally described herein. For example, in one embodiment, the apparatus 100 can provide a menu from which the annotator can select a suitable tool or utility to annotate the image 400, including the grid-lines 402, control points 412 and contour 410.

The processor 102 is configured to set the initial contour 410 and the control points 412 based on the partitioning. The partitioning process uses a suitable algorithm to identify the edges of the object of interest 406. The initial contour 410 and control points 412 are used to provide a visual demarcation of the edges as identified by the partitioning algorithm.

In one embodiment, the granularity or fineness of the partitioning shown in FIG. 4A can be varied. The closer together the grid lines are positioned, the finer the granularity of the partitioning. Such granularity can be used to provide more definition to the contour 406. For example, finer granularity in the grid lines can enhance the detection of edges of the object(s) of interest by the partitioning algorithm. In one embodiment, the granularity or fineness of the partitioning can be set or adjusted by the user.

As shown in the example of FIG. 4A and 4B, the processor 102 is configured to generate an initial contour 410 for the object of interest 406. In the example of FIG. 4B, the initial contour 410 is identified by one or more control points 412 positioned on or near the grid lines 402. The aspects of the disclosed embodiments are configured to differentiate between the light and dark areas and identify the edges of the object of interest 406. The control points 412 are then disposed on or in conjunction with the grid lines that one or more of form or are closest to the edges, such as grid line 402a and 402b.

The control points 412, also referred to as markers 412, are generally configured to provide identification points along the edges or boundaries of the object of interest 406. In some cases, manual adjustment of one or more of the control points 412 is required in order to more accurately identify the edges. For example, as illustrated in FIG. 4B, one or more of the control points 412, such as control points 412a and 412b, may not be accurately located with respect to the edges or boundary of the object of interest. In this example, control points 412a and 412b are associated with or connected by grid line 402b. However, a more accurate placement or connection of the control points 412a and 412b may be grid line 402c. The aspects of the disclosed embodiments are configured to enable the annotator to manually reposition one or more of the control points 412 as well as redefine the initial contour 410 relative to the grid lines 402.

Figure 5:
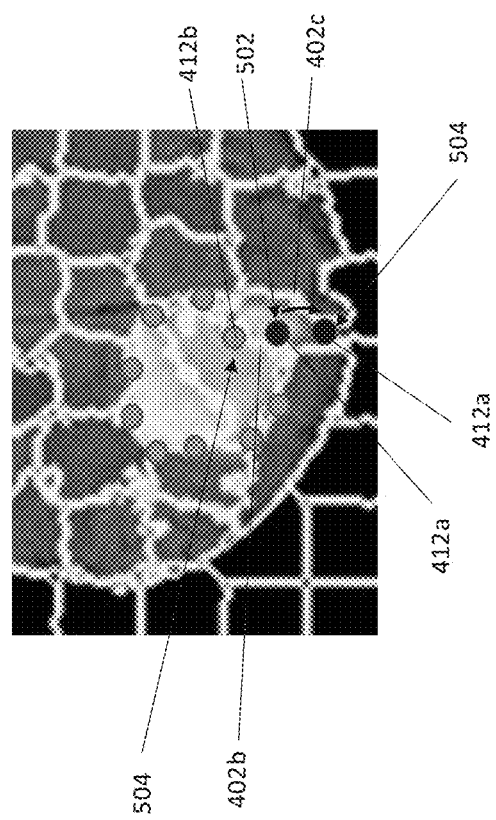
FIG. 5 illustrates one example of the manual adjustment or movement of a control point on the partitioned medical image data of FIG. 4A.

FIG. 5 illustrates one example of an image 510 showing the manual repositioning of a control point 412. In this example, the control point 412a is manually repositioned from an initial position 502 to a next position 504. In this manner, the control point 412a is more closely associated with grid line 402c. In this example, the grid line 402 may be more accurately associated with the edge of the object of interest 406 than the grid line 402b. Although only one control point 412a is shown as manually adjusted, the aspects of the disclosed embodiments are not so limited. In alternate embodiments, any suitable number of control points 412 can be adjusted.

Figure 6:
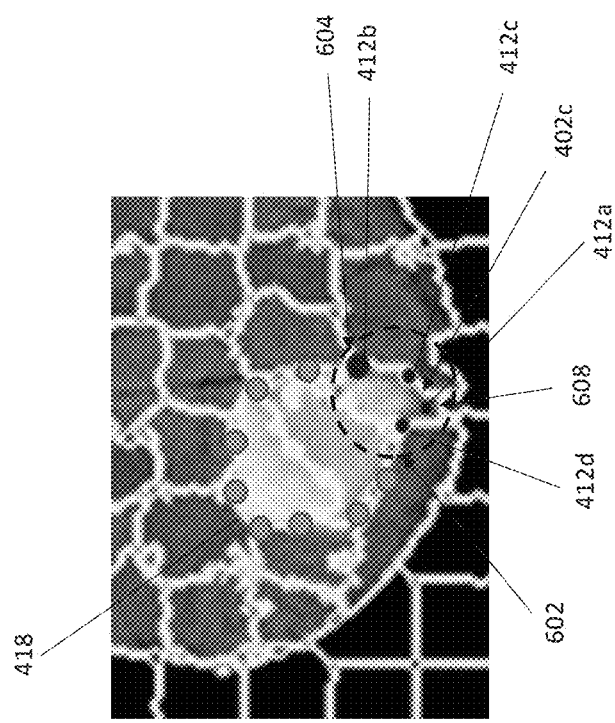
FIG. 6 illustrates one example of the automatic adjustment of adjacent control points in accordance with the aspects of the disclosed embodiments.

FIG. 6 illustrates the automatic adjustment of adjacent or nearby control points and the contour in accordance with the aspects of the disclosed embodiments. As noted with respect to FIG. 5, control point 412a was manually adjusted from position 502 to position 504. In accordance with the aspects of the disclosed embodiments, the positions of control points that are one or more of adjacent to or within a predetermined distance from the manually adjusted control point are automatically adjusted and updated.

An "adjacent control point" as that term is used herein, generally refers to a control point 412 that is within a certain distance or range of the manually adjusted control point, which is control point 412a in the example of FIGS. 5 and 6. Although the term "adjacent" is used herein, the aspects of the disclosed embodiments are intended to apply to any control point that is within the predetermined range or area of the manually adjusted control point. In one embodiment, the predetermined distance, range or area can be manually set or adjusted by the user/annotator.

In the example of FIG. 6, area 602 is defined as the area of control points adjacent to the manually adjusted control point 412a. In this example, control point 412b is automatically adjusted from its position 504 shown in FIG. 5 to a new position 604 as shown in FIG. 6. The new position 604 in this example is associated with grid line 402c.

In one embodiment, the adjustment of the control point 412b is based on a degree of movement of the manually adjusted control point 412a. For example, the determination of the new location 604 for the control point 412b can be proportional to the distance of the movement of the manually adjusted control point 412a.

In one embodiment, the movement of the control point 412b will be to the next closest grid line, relative to the movement of the manually adjusted control point 412a. In the example of FIG. 6, control point 412b moves from grid line 402b to grid line 402c, in a direction and distance relative to the direction and distance of the adjustment of control point 412a.

As shown in FIG. 6, in addition to the adjustment of control point 412b, additional control points 412c and 412d can be generated. The additional control points 412c and 412d are disposed on the grid lines connecting the respective control points to the repositioned control point 412a. For example, control point 412c is positioned on grid line 402c connecting control point 412a and 412c.

The automatic repositioning of the adjacent control points results in the generation or definition of an adjusted or new contour line, generally illustrated as contour line 608 in FIG. 6. As shown in this example, the aspects of the initial contour lines 410 of FIG. 4B are modified or changed in the area 602 of FIG. 6, relative to the manual adjustment of control point 412a. In the example of FIG. 4B, the initial contour line 410 was associated with grid line 402b. As shown in FIG. 6, the updated contour line 608 is now associated with grid line 402c.

Figure 7:
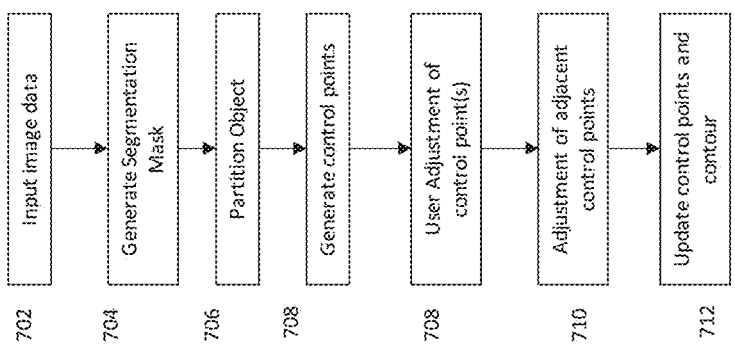
FIG. 7 is a flowchart illustrating an exemplary process flow incorporating aspects of the disclosed embodiments.

FIG. 7 is a flow chart illustrating one embodiment of a process incorporating aspects of the disclosed embodiments. In one embodiment, image data is input 702. This can include a sequence of images. A segmentation mask is generated 704. A partition is then applied 706. Control points are generated 706 on an initial contour relative to the object of interest.

In one embodiment, a manual adjustment of at least one control point is identified or detected 708. Adjacent or nearby control points are identified and positions of the adjacent control points are automatically adjusted 710 relative to the movement of the manually adjusted control point. Updated control points and contour are generated 712 for visualization by the user and/or annotator. This can include, for example, the display of an image with the updated control points and contour.

In one embodiment, the apparatus 100 shown in FIG. 1, generally comprises a computing device. The computing device can comprise or include any suitable computer or computing arrangement.

In one embodiment, the processor 102 comprises a hardware processor. Although only one processor 102 is generally described herein, the aspects of the disclosed embodiments are not so limited. In alternate embodiments, the apparatus 100 can include any suitable number of processors 102.

Referring again to FIG. 1, the apparatus 100 generally includes suitable logic, circuitry, interfaces and/or code that is configured to receive the input image data 108 and process the image data 108 as is generally described herein. In some embodiments, the processor 102 can be configured to receive a sequence of image frames (e.g., one or more video) of the patient from the imaging system 110. The imaging system 110 will generally include suitable image capture devices or sensors.

The processor 102 generally includes suitable logic, circuitry, interfaces and/or code that is configured to process the image input data 108 as is generally described herein. The processor 102 is configured to respond to and process instructions that drive the apparatus 100. Examples of the processor 102 include, but are not limited to, a microprocessor, a microcontroller, a complex instruction set computing (CISC) microprocessor, a reduced instruction set (RISC) microprocessor, a very long instruction word (VLIW) microprocessor, or any other type of processing circuit. Optionally, the processor 102 may be one or more individual processors, processing devices and various elements associated with a processing device that may be shared by other processing devices. Additionally, the one or more individual processors, processing devices and elements are arranged in various architectures for responding to and processing the instructions that drive the system 100. The apparatus 100 can include any suitable components or devices that are needed to carry out the processes described herein, such as a memory or storage, for example.

In one embodiment, the apparatus 100 can comprise or be part of a standalone computing device, in communication with, or part of, the imaging system 110. In one embodiment, the apparatus 100 will include or be connected to the machine learning models needed to carry out the aspects of the disclosed embodiments described herein.

In the example of FIG. 1, the apparatus 100 also includes or is communicatively coupled to a memory 104. Although not shown, the apparatus 100 could be communicatively coupled to network or network interface to enable communication with the components and devices of the apparatus 100 and image system 110.

The memory 104 may comprise suitable logic, circuitry, interfaces, and/or code that may be configured to store instructions executable by the processor 102. The memory 104 is further configured to store the image data 108. The memory 104 may be further configured to store operating systems and associated applications of the processor 102. Examples of implementation of the memory 104 may include, but are not limited to, Random Access Memory (RAM), Read Only Memory (ROM), Hard Disk Drive (HDD), Flash memory, and/or a Secure Digital (SD) card. A computer readable storage medium of a computer program product for providing a non-transient memory may include, but is not limited to, an electronic storage device, a magnetic storage device, an optical storage device, an electromagnetic storage device, a semiconductor storage device, or any suitable combination of the foregoing.

The aspects of the disclosed embodiments are directed to an interactive contour refinement process for efficient data annotation. The positions of one or more control points on a contour are automatically adjusted relative to a manual adjustment of another control point on the contour. Implementation of the aspects of the disclosed embodiments can be in the form of a portal or software installed in a computer that can read/load/store sensor data (e.g., CT/MRI scans), display images and provide tools to the annotator(user) for them to annotate images. The output can be a binarized mask generated by the control points and contour lines.

Various embodiments and variants disclosed above, with respect to the aforementioned system 100, apply mutatis mutandis to the method. The method described herein is computationally efficient and does not cause processing burden on the processor 102.

Modifications to embodiments of the aspects of the disclosed embodiments described in the foregoing are possible without departing from the scope of the aspects of the disclosed embodiments as defined by the accompanying claims. Expressions such as "including", "comprising", "incorporating", "have", "is" used to describe and claim the aspects of the disclosed embodiments are intended to be construed in a non-exclusive manner, namely allowing for items, components or elements not explicitly described also to be present. Reference to the singular is also to be construed to relate to the plural.

Thus, while there have been shown, described and pointed out, fundamental novel features of the invention as applied to the exemplary embodiments thereof, it will be understood that various omissions, substitutions and changes in the form and details of devices and methods illustrated, and in their operation, may be made by those skilled in the art without departing from the spirit and scope of the presently disclosed invention. Further, it is expressly intended that all combinations of those elements, which perform substantially the same function in substantially the same way to achieve the same results, are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. An apparatus for image data annotation, the apparatus comprising at least one hardware processor configured to:
   obtain image data;
   partition the image data;
   identify an object of interest in the partitioned image data;
   generate an initial contour with one or more control points with respect to the object of interest;
   identify a manual adjustment of one of the one or more control points;
   automatically adjust a position of at least one other control point within a predetermined range of the manually adjusted control point to a new position, wherein the automatic adjustment comprises repositioning the at least one other control point to a next grid line that is closest to a current grid line associated with the at least one other control point and in a direction of movement of the manually adjusted control point, and wherein the new position of the at least one other control point and the manually adjusted control point define a new contour; and
   generate an updated image with the new contour and corresponding control points.

2. The apparatus according to claim 1, wherein the at least one hardware processor is configured to generate a segmentation mask from the obtained image data, the segmentation mask being configured to identify the object of interest.

3. The apparatus according to claim 1, wherein the at least one hardware processor is configured to adjust the position of the at least one other control point in a same direction as a direction of movement of the manually adjusted control point.

4. The apparatus according to claim 1, wherein the at least one hardware processor is configured to automatically adjust the position of the at least one other control point by an amount that is proportional to a movement of the manually adjusted control point.

5. The apparatus according to claim 1, wherein the position of the at least one other control point is adjacent to a position of the manually adjusted control point.

6. The apparatus according to claim 1, wherein the at least one hardware processor is further configured to determine a granularity of a fineness of the partition of the image data and adjust the position of the at least one other control point based on the determined granularity.

7. The apparatus according to claim 1, wherein the adjustment of the position of at least one other control point is a pixel based adjustment.

8. The apparatus according to claim 1, wherein the image data includes one or more of a red-green-blue image, a depth image, a thermal image or a medical scan image.

9. The apparatus according to claim 1, wherein the partitioning of the image data comprises generating multiple non-linear grid lines associated with the object of interest, the multiple non-linear grid lines comprising the current grid line associated with the at least one other control point and the next grid line that is closest to the current grid line.

10. The apparatus according to claim 1, wherein the apparatus comprises a medical imaging device.

11. A computer implemented method, comprising:
    obtaining image data;
    partitioning the image data;
    identifying an object of interest in the partitioned image data;
    generating an initial contour with one or more control points with respect to the object of interest;
    identifying a manual adjustment of one of the one or more control points;
    automatically adjusting a position of at least one other control point within a predetermined range of the manually adjusted control point to a new position, wherein the automatic adjustment comprises repositioning the at least one other control point to a next grid line that is closest to a current grid line associated with the at least one other control point and in a direction of movement of the manually adjusted control point, and wherein the new position of the at least one other control point and the manually adjusted control point define a new contour; and
    generating an updated image with the new contour and corresponding control points.

12. The computer implemented method according to claim 11, wherein the method further comprises generating a segmentation mask for the image data, the segmentation mask identifying the object of interest.

13. The computer implemented method according to claim 11, further comprising adjusting the position of the at least one other control point in a same direction as a direction of movement of the manually adjusted control point.

14. The computer implemented method according to claim 11, the method further comprising automatically adjusting the position of the at least one other control point by an amount that is proportional to a movement of the manually adjusted control point.

15. The computer implemented method according to claim 11, wherein the position of the at least one other control point is adjacent to a position of the manually adjusted control point.

16. The computer implemented method according to claim 11, the method further comprising determining a granularity of a fineness of the partition of the image data and adjusting the position of the at least one other control point based on the determined granularity.

17. The computer implemented method according to claim 11, wherein the partitioning of the image data comprises generating multiple non-linear grid lines associated with the object of interest, the multiple non-linear grid lines comprising the current grid line that is associated with the at least one other control point and the next grid line that is closest to the current grid line.

18. A computer program product comprising a non-transitory computer-readable medium having machine-readable instructions stored thereon, which when executed by a computer causes the computer to execute the method according to claim 11.

* * * * *